United States Patent [19]

Labarre

[11] Patent Number: 5,718,907
[45] Date of Patent: Feb. 17, 1998

[54] PROCESS FOR THE PREPARATION OF ORGANOPHILIC METAL OXIDE PARTICLES

[75] Inventor: Dominique Labarre, Neuilly-sur Seine, France

[73] Assignee: Rhone-Poulenc Chimie, Courbevoie Cedex, France

[21] Appl. No.: 494,732

[22] Filed: Jun. 26, 1995

[30] Foreign Application Priority Data

Jun. 24, 1994 [FR] France .................... 94 07832

[51] Int. Cl.$^6$ ............... A61K 9/10; B01J 13/00; B05D 7/00; C08K 3/22
[52] U.S. Cl. ............... 424/401; 106/447; 252/309; 252/315.2; 424/70.9; 427/214; 427/220; 428/405; 514/972; 524/403; 524/413
[58] Field of Search ............... 252/309, 315.2; 427/214, 220; 428/405; 424/70.9, 401; 514/972; 524/403, 413; 106/436, 437, 447

[56] References Cited

U.S. PATENT DOCUMENTS

| | | | |
|---|---|---|---|
| 3,920,865 | 11/1975 | Läufer et al. | 427/220 |
| 4,068,024 | 1/1978 | Laufer | 427/220 |
| 4,522,958 | 6/1985 | Das et al. | 523/212 |
| 4,740,423 | 4/1988 | Kadokura et al. | 428/403 |
| 4,782,040 | 11/1988 | Revis et al. | 428/405 X |
| 4,937,104 | 6/1990 | Pühringer | 427/344 |
| 5,013,585 | 5/1991 | Shimizu et al. | 427/220 |
| 5,372,905 | 12/1994 | Deusser et al. | 428/405 X |
| 5,501,732 | 3/1996 | Niedenzu et al. | 106/447 |

FOREIGN PATENT DOCUMENTS

| | | |
|---|---|---|
| 0216047 | 7/1986 | European Pat. Off. |
| 0523654 | 7/1992 | European Pat. Off. |
| 211018 | 11/1971 | France. |
| 1154835 | 3/1966 | United Kingdom. |
| 1376706 | 3/1973 | United Kingdom. |

OTHER PUBLICATIONS

Chemical Abstracts, vol. 94, No. 6, Feb. 9, 1981, Columbus, Ohio, US; Abstract No. 32299m, p. 90; col. L; JP-A-80 110 163 (Malvern Minerals), Aug. 25, 1980.

*Primary Examiner*—Richard D. Lovering
*Attorney, Agent, or Firm*—Burns, Doane, Swecker & Mathis, L.L.P.

[57] ABSTRACT

Organophilic particles of a metal oxide chosen from alumina $Al_2O_3$, silica $SiO_2$, transition metal oxides, especially titanium oxide $TiO_2$, and rare-earth metal oxides, especially cerium oxide $CeO_2$, are prepared by reacting an aqueous-alcoholic suspension (a) of metal oxide particles which have no pores less than 5 nm in di-meter at their surface with an anhydrous alcoholic solution (b) comprising at least one alkoxysilane of formula (1)

$$Si(OR)_xR'_{4-x} \qquad (1)$$

in which R represents an alkyl group containing from 1 to 6 carbon atoms, R' represents a hydrocarbon group chosen from alkyl, cycloalkyl, aryl, alkylaryl, arylalkyl, alkenyl and alkynyl groups containing at least one carbon atom and x is an integer from 1 to 3, the said alcohols, which may be identical or different, containing from 1 to 5 carbon atoms.

34 Claims, No Drawings

PROCESS FOR THE PREPARATION OF ORGANOPHILIC METAL OXIDE PARTICLES

The present invention relates to a process for preparation of organophilic metal oxide particles.

It is common to use inorganic particles as filler, pigment or additive in fields as diverse as paints, plastics or cosmetics. Problems arise when these inorganic hydrophilic particles have to be incorporated into solid or liquid organic matrices, since their low affinity for such media is reflected in a poor dispersion in the matrix.

However, the efficiency of the pigment or of the filler is optimal when the particles are in a maximum state of dispersion. Efforts are thus made to obtain particle suspensions as dispersed as possible.

In order to be dispersible, the particle must be "wettable" by the matrix, that is to say that its surface must be made compatible with the organic matrix.

In practice, a so-called "compatibilizing" agent is introduced into the organic suspension, this agent interacting with the particles to make the suspension stable. The particles thus incorporated into the organic matrix are often agglomerated, and the state of dispersion is improved by deagglomerating the suspension by adding thereto an agent for the steric stabilization of the particles. By forming a coating of a few nanometers around the compatibilized inorganic particle, such a molecule facilitates the dispersion of deagglomerated particles.

Thus, dispersions of inorganic particles in organic medium are conventionally obtained by blending/grinding the inorganic support in an organic solvent in the presence of a surfactant molecule which acts both as a wetting agent and as a steric stabilizing agent (the carbon chain hanging from the surfactant molecule being sufficient to form a coating on the particle). However, when the inorganic particles are of nanometric size (that is to say when they are smaller than 0.1 µm in diameter), it is difficult to achieve a maximum state of dispersion by this mode of treatment.

Moreover, the interaction between the surface of the mineral and the compatibilizing molecule, which may for example be a fatty acid, a fatty alcohol or an anionic surfactant, has a relatively pronounced reversible nature which results in a certain instability of the dispersion.

It is preferred to establish an irreversible interaction between the compatibilizing agent and the inorganic particle by forming a covalent bond between a reactive site of the particle and a reactive function of the compatibilizing molecule. The inorganic particle thus modified is made irreversibly organophilic and can be isolated, and subsequently used easily for any application in organic medium.

The present invention falls within this context, since its aim is to provide a process for the preparation of organophilic inorganic particles which are dispersible in an organic solvent.

Indeed, the present inventors have discovered that when hydrophilic metal oxide particles are compatibilized by grafting alkylsilane groups onto the surface in an aqueous-alcoholic medium, it is possible to arrive at final particles which are highly dispersible in organic medium if "non-nanoporous" starting oxide particles, that is to say particles not having any pores less than 5 nm in diameter at their surface, are used.

The subject of the present invention is thus a process for the preparation of organophilic particles of a metal oxide chosen from alumina $Al_2O_3$, silica $SiO_3$, transition metal oxides, especially titanium oxide $TiO_2$, and rare-earth metal oxides, especially cerium oxide $CeO_2$, in which process an aqueous-alcoholic suspension (a) of metal oxide particles which have no pores less than 5 nm in diameter at their surface is reacted with an anhydrous alcoholic solution (b) comprising at least one alkoxysilane of formula (1)

$$Si(OR)_xR'_{4-x} \quad (1)$$

in which R represents an alkyl group containing from 1 to 6 carbon atoms, R' represents a hydrocarbon group chosen from alkyl, cycloalkyl, aryl, alkylaryl, arylalkyl, alkenyl and alkynyl groups containing at least one carbon atom and x is an integer from 1 to 3, the said alcohols, which my be identical or different, containing from 1 to 5 carbon atoms.

This process may be applied in particular to metal oxide "nanoparticles", that is to say to particles having a mean diameter less than or equal to 100 nm. The standard compatibilization processes employed to date do not make it possible to impart to these small particles the good dispersibility properties obtained by the process according to the invention, and which will he evidenced below.

In the case where the oxide particles to be treated are "nanoporous", that is to say that they have pores less than 5 nm in diameter at the surface, the process includes a preliminary step which consists in removing this nanoporosity.

This preliminary step may comprise a heat treatment of the nanoporous particles in an autoclave. Such a treatment is described especially in Patent Application FR-A-2,677,012 filed by the Applicant.

It is also possible to carry out, a chemical treatment of the nanoporous particles. In that case, particles are suspended in an aqueous—alcoholic medium the alcohol containing from 1 to 5 carbon atoms, and the suspension (c) thus obtained is reacted with at least one tetraalkoxysilane of formula (2)

$$Si(OR'')_4 \quad (2)$$

in which R" represents an alkyl group containing from 1 to 5 carbon atoms.

The tetraalkoxysilane is added in small portions to the suspension. After the treatment, a stable aqueous-alcoholic suspension (a) of non-nanoporous inorganic particles is obtained, which suspension (a) can then be treated directly with an alkoxysilane of formula (1) as indicated above for the actual compatibilization.

In the case where non-nanoporous particles in powder form are available, the compatibilization is carried out directly. The particles are suspended in an aqueous-alcoholic medium in order to obtain an inorganic sol (a).

In the aqueous-alcoholic medium of the suspension (a), an alkoxysilane of formula (1) is hydrolysed to a silanol which is capable of condensing with one or more hydroxyl functions present at the surface of the metal oxide.

The overall reaction for the compatibilization (grafting) may thus be described in simple terms as the combining of the following two reactions:

1—hydrolysis of the alkoxysilane $$\equiv SiOR + H_2O \rightarrow \equiv SiOH + ROH$$
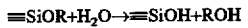

2—condensation of the silanol obtained on the surface of the oxide $$\equiv MOH + \equiv SiOH \rightarrow \equiv M-O-Si \equiv + H_2O$$
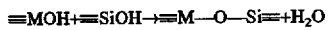

Many silicon compounds may be envisaged to carry out such a grafting by hydrolysis/condensation, but not all can be used under the reaction conditions of the process according to the invention.

The alkoxysilanes of formula (1) defined above are well suited to carrying out the process of the invention, since they are soluble in the grafting medium and are not hydrolysed too quickly in this medium.

A silicon compound which has a great tendency to hydrolyse would be liable to condense with itself and not with the surface hydroxyl functions of the mineral. This is the case, for example, of a disilazane.

This drawback is avoided by selecting alkoxysilanes of formula (1) whose reactivity is moderate.

Among the compounds of formula (1), it is preferable for the radical R to represent a methyl or ethyl group.

Similarly, it is advantageous for R' to represent an octyl, dodecyl or octadecyl group.

Moreover, trialkoxysilanes, that is to say compounds such that x=3, are preferred.

By way of example, there may be mentioned octyltrimethoxysilane (OTMS), dodecyltrimethoxysilane (DTMS) or n-octadecyltrimethoxysilane (ODTMS).

Among the metal oxides, there may in particular be mentioned titanium oxide, which is used in rutile or anatase form. This may especially be lenticular or platelet anatase.

According to the process of the invention, an aqueous-alcoholic suspension (a) of non-nanoporous metal oxide particles is prepared. The oxide particles disperse readily in the medium.

The weight ratio of the water to the alcohol in this suspension is advantageously between 0.2 and 0.8.

The process is preferably performed with a dilute suspension and the concentration by weight of the particles in this suspension is preferably between 5 g/l and 200 g/l.

The aqueous-alcoholic suspension (a) may be acidic or basic and its pH varies depending on the oxide to be treated.

In general, when the process is performed in a basic medium, the pH is advantageously between 9 and 12. The base used to set this pH may be chosen from hydroxides of alkali metals and especially sodium, lithium and potassium-hydroxides; carbonates of alkali metals, and especially sodium and potassium carbonates; aqueous ammonia and primary, secondary or tertiary amines, such as monoethylamine or diethylamine.

In particular, it is preferable for the pH to be above IEP+2, where IEP is the isoelectric point of the oxide to be treated.

In general, when the process is performed in acidic medium, the pH, is advantageously between 1 and 5. The acid used to set the pH may be chosen from nitric acid, hydrochloric acid, acetic acid and other organic acids.

In particular, it is preferable for the pH to be below IEP-2, where IEP is the isoelectric point of the oxide to be treated.

An anhydrous alcoholic solution (b) comprising at least one alkoxysilane of formula (1) is then added at a low flow rate, care being taken to maintain the dispersion of the materials in the reaction medium. This makes it possible to avoid the residual risks of self-condensation of the alkoxysilane(s).

The alcohol of the solution (b) is preferably identical to that of the aqueous-alcoholic suspension (a).

The provision of alkoxysilane varies as a function of the size of the oxide particles to be treated and the weight ratio of the total amount of alkoxysilane (1) to the amount of oxide may be from 1 to 60%.

The temperature of the reaction medium during this addition is advantageously between 15° and 70° C., and is preferably room temperature.

During the addition, flocculation occurs in the suspension, indicating a change in the interface properties of the oxide particles.

After the addition, it is preferable to allow the reaction to continue for one to two hours.

Once the reaction is complete, the compatibilized particles may be isolated either in powder form or in organic suspension form by stirring with an organic In order to obtain a powder, the reaction mixture is subjected to a liquid/solid separation, advantageously by centrifugation. The solid separated is washed with alcohol and then dried at low temperature, for example at about 60° C.

When grafting of the alkoxysilane (1) has taken place in ammoniacal medium, the reaction mixture is preferably subjected to a step of distillation at low temperature in order to remove the ammonia and the alcohol, prior to the solid/liquid separation.

The powder obtained may then be suspended in an organic medium.

It has moreover been observed that if the reaction mixture is stirred with an organic liquid chosen from a natural or synthetic oil, a hydrocarbon solvent or any water-immiscible solvent, the compatibilized particles migrate spontaneously to the organic medium, on account of their organophilic nature.

By exploiting this property, one variant of the preparation process according to the invention has been developed, this variant consisting in reacting the aqueous-alcoholic suspension (a) of metal oxide particles with an alcoholic solution (b) comprising at least one alkoxysilane (1) in the presence of a water-immiscible organic liquid, such that the reaction takes place in a two-phase medium. Thus, as the compatibilization reaction proceeds, the particles which have reached a sufficient degree of hydrophobicity pass spontaneously into the organic phase in which they are readily dispersible. The particles may be isolated and dried, but this procedure makes it especially possible directly to obtain good dispersions in organic medium.

An organic suspension of compatibilized oxide particles may thus readily be obtained by doing away with the steps of separation, washing and drying, if the process is performed in the presence of an organic liquid throughout the reaction or indeed simply at the end of the compatibilization reaction.

In the case of a cosmetic application, the preferred organic liquid for performing this operation is an oil and in particular isopropyl palmirate.

The organophilic particles prepared according to the process of the invention have an excellent affinity for organic media and good dispersibility in these media.

Advantageously, the state of dispersion of an organic suspension containing the said compatibilized particles is improved by adding to the suspension a steric stabilizing agent such as a nonionic surfactant. This surfactant has the effect of stabilizing the highly dispersed suspension.

Among these surfactants, there may especially be mentioned ethoxylated alkylphenols and in particular ethoxylated nonylphenol.

The suspensions my also be redispersed mechanically using ultrasound, in order to maintain an optimum state of dispersion of the compatibilized particles.

An organic sol containing the compatibilized particles according to the invention has a state of dispersion close to that of the starting aqueous-alcoholic mineral sol.

This state of dispersion may be estimated by exploiting the properties of absorption of ultraviolet light by the suspensions of oxide particles considered.

The compatibilized particles are dispersed in hexane, by adding a stabilizing agent in order to obtain a stable sol, and the ratio between the absorbance in the ultraviolet region at 308 nm and the absorbance in the visible region at 525 nm: $A_{308}/A_{525}$, is then measured for this dispersion. The higher this ratio, the more transparent this suspension will be in the visible region and the more absorbent it will be in the UV region, the absorbance in the UV region being linked to the presence of oxide particles and the transparency in the visible region, to the state of dispersion of the particles in the suspension.

This ratio is finally compared with that obtained for a dispersion in water of starting, non-compatibilized and thus hydrophilic particles, the state of dispersion of which represents the maximum which can be achieved. A compatibilization treatment is considered to be all the more mediocre that the value of the ratio $A_{308}/A_{525}$ measured for the organic dispersion is low as compared to that of the aqueous sol of starting particles. This treatment is considered to be optimal when the value of the ratio $A_{308}/A_{525}$ measured for the organic dispersion is greater than or equal to that corresponding to the aqueous sol of starting particles.

It is observed that the organic dispersions of organophilic particles prepared by a process according to the invention have a state of dispersion which is comparable with, or even equal to, the state of dispersion of the aqueous sol of hydrophilic starting particles. The organic suspensions may thus be classed as being "highly dispersed".

The high dispersibility of the organophilic particles prepared according to the invention makes them particularly suited to all the applications of metal oxides in organic medium, for example as a reinforcement filler for materials.

It is advantageously possible to exploit the properties of absorption of ultraviolet rays by the organic dispersions of organophilic oxide particles obtained by a process described above.

Thus, the invention also relates to the use of these organophilic metal oxide particles as anti-UV agent in plastics such as polyethylene or polypropylene. The good dispersion of the particles within the polymer matrix allows the optical properties of the unfilled polymer to be retained. Moreover, the anti-UV effect of the present oxide particles is comparable to that obtained with standard organic anti-UV agents.

In particular, the compatibilized titanium oxide nanoparticles have properties of permanence in plastics, in contrast with monomeric organic anti-UV agents which, over time, migrate to the surface of the film and thus lose their activity. Polymeric organic anti-UV agents themselves migrate little or not at all, but this occurs to the detriment of their anti-UV performance. The compatibilized $TiO_2$ nanoparticles according to the invention thus optimize the balance between anti-UV efficiency and permanence in the plastic.

In addition, the cerium or titanium oxide particles rendered organophilic may also be used as anti-UV agent in liquid or solid organic cosmetic products. The oxide powders and the organic dispersions of these organophilic particles have, indeed, a very weak absorption in the visible region and a very strong absorption in the ultraviolet region. When incorporated into a cosmetic formulation, especially in cream or powder form, they make it possible to obtain products which, when spread on the skin, are transparent and yet highly protective against ultraviolet rays.

It should also be noted that the organophilic oxide particles are perfectly hydrophobic and chemically inert.

Indeed, untreated metal oxides, in particular of titanium, have a strong tendency to degrade the surrounding organic molecules.

In the present case, it is thought that the alkoxysilane graft (1) forms a coating which protects the surface of the inorganic oxide.

The particles obtained according to the invention thus represent particularly advantageous fillers or additives which do not promote the degradation of the final product in which they are incorporated.

The invention is thus also directed to the organophilic particles and the organophilic particle suspensions obtained by a process described above.

The present invention is illustrated by the following examples:

EXAMPLES

Example 1

In this example, the particles to be treated are titanium oxide particles in platelet anatase form obtained by hydrothermal synthesis and autoclaving. These monocrystalline particles have a size approaching about ten nanometers and are highly aggregated (size of the aggregates=100 to 200nm). The surface of the particles contains no pores smaller than 5 nm.

A base stock is prepared in a reactor, stirred at 500 revolutions per minute, by mixing together, at 25° C., 400 ml of deionized water, 600 ml of pure ethanol and 10 g of titanium oxide. The pH of the aqueous-alcoholic suspension is adjusted to 2 by adding the required amount of nitric acid.

A solution containing 1.6 g of octyltrimethoxysilane in 50 ml of ethanol is added at a flow rate of 15 ml/hour to the base stock. After the addition, a flocculated suspension is obtained which sediments in the reactor.

100 ml of isopropyl palmirate are poured into the flocculated suspension and, after stirring, it is observed that the solid passes into the organic phase. The oily suspension is separated and 10% of 9EO ethoxylated nonylphenol (CEMULSOL NP9) is added thereto in order to stabilize it.

The suspension remains stable for several weeks.

In order to characterize the dispersibility of the compatibilized particles, the same reaction is carried out but the sedimented solid is separated after the addition of OTMS. This solid is washed with alcohols and then dried at 60° C.

A suspension of this solid is prepared in hexane in the presence of ethoxylated nonylphenol, and the absorbance of this suspension in the ultraviolet region at 308 nm ($A_{308}$) and in the visible region at 525 nm ($A_{525}$) are then measured.

The ratio $A_{308}/A_{525}$, which indicates the state of dispersion of the suspension, is compared with the same ratio corresponding to an aqueous suspension of non-compatibilized oxide particles, which serves as reference as a perfectly dispersed suspension.

For the organic suspension of compatibilized particles, $(A_{308}/A_{525})_{org}$ is equal to 2.4.

For the aqueous sol of noncompatibilized starting particles, $(A_{308}/A_{525})_{aq}$ is equal to 2.5.

The ratio $(A_{308}/A_{525})_{org}$ is very slightly smaller than the ratio for the aqueous reference, which indicates that the dispersibility of the compatibilized particles in organic medium is excellent.

The solid particles prepared according to this procedure are subjected to a hydrophobicity test on dry product. After placing a drop of water on the powder, it is observed that the drop does not spread out and remains in the form of a spherical drop.

The degree of protection of the oxide surface is also evaluated, by means of a colorimetric test. The tendency of the compatibilized particle to degrade an organic medium is thus estimated.

A little powder is blended with a few drops of an $H_2SO_4$—$H_2O_2$ mixture. A colour ranging from pale yellow to blood red and corresponding to the $TiO_2^{2+}$ complex is then developed more or less rapidly. The quality of the coating is graded from the colour developed after a well defined period.

| Colour developed | Red-orange | Orange-red | Golden yellow | Pale yellow |
|---|---|---|---|---|
| Classification of the degree of protection | 0 poor protection | + | ++ | +++ very good protection |

According to this test, the particles of Example 1 have a good surface protection (++).

Example 2

In this example, the particles to be treated are titanium oxide particles in lenticular anatase form (obtained by thermal hydrolysis of titanium oxychloride in the presence of citric acid). These polycrystalline particles (size of crystallite≈6 nm) are 30 to 50 nm in diameter, and are well individualized. Porosity measurements showed that these lenticular anatase particles have pore sizes smaller than 5 nm In a first step, a pretreatment consisting in removing this nanoporosity is thus performed.

A base stock is prepared, in a reactor stirred at 500 revolutions/minute, by mixing, at 25° C., 240 ml of deionized water, 500 ml of pure ethanol, 260 ml of aqueous ammonia solution containing 25% of $NH_3$ and 10 g of titanium oxide.

The surface pretreatment is carried out by adding, at a flow rate of 15 ml/h, a solution containing 12 g of tetraethyl orthosilicate in 50 ml of ethanol. After the addition, a stable suspension is obtained.

The compatibilization is then carried out by adding, at a flow rate of 15 ml/h, a solution containing 5 g of octyltrimethoxysilane in 10 ml of ethanol. At the end of the reaction, a flocculated suspension is obtained which sediments in the reactor.

100 ml of isopropyl palmirate are poured into the flocculated suspension and, after stirring, the solid passes into the organic phase. The oily suspension is separated and 10% of ethoxylated nonylphenol (CEMULSOL NP9) is added thereto.

The suspension remains stable for several weeks.

The dispersibility of the compatibilized particles is characterized as in Example 1.

For the organic suspension of compatibilized particles, $(A_{308}/A_{525})_{org}$ is equal to 9.

For the aqueous sol of noncompatibilized starting particles, $(A_{308}/A_{525})_{aq}$ is equal to 8.5.

The dispersibility of the compatibilized particles is excellent.

The compatibilized particles of Example 2 exhibit perfect hydrophobicity and very good surface protection (+++) according to the colorimetric test.

COMPARATIVE EXAMPLE

By way of comparison, the treated nanoporous lenticular anatase particles in Example 2 are subjected directly to the compatibilization with octyltrimethoxysilane, without performing the surface pretreatment intended to remove the nanoporosity.

A base stock is prepared in a reactor stirred at 500 revolutions/minute by mixing, at 25° C., 240 ml of deionized water, 500 ml of pure ethanol, 260 ml of aqueous ammonia solution containing 25% of $NH_3$ and 10 g of the said nanoporous titanium oxide particles.

A solution containing 5 g of octyltrimethoxysilane in 10 ml of ethanol is added to this base stock at a flow rate of 15 ml/h. At the end of the reaction, a flocculated suspension is obtained which sediments in the reactor.

As in Example 2, isopropyl palmitate is added to the flocculated suspension, but, even after very vigorous stirring, it is not possible to make the solid pass into the organic phase.

The solid is separated from the reaction medium by settling, washed with ethanol and dried at 60° C.

The dispersibility of the particles is assessed by suspending them in hexane in the presence of ethoxylated nonylphenol (CEMULSOL NP9), as in Example 1. For this organic suspension of non-pretreated compatibilized particles, the ratio $(A_{308}/A_{525})_{org}$ is equal to 3.9 whereas, for the aqueous sol of noncompatibilized nanoporous starting particles, the ratio $(A_{308}/A_{525})_{aq}$ is equal to 8.5 and, for the organic sol of pretreated and compatibilized particles of Example 2, the ratio $(A_{308}/A_{525})_{org}$ is equal to 9.

The ratio $(A_{308}/A_{525})_{org}$ of the non-pretreated compatibilized particles is considerably smaller than the ratio for the aqueous reference, which indicates that the dispersibility in organic medium of the compatibilized, but still nanoporous, particles is very poor.

As a guide, the ratio $(A_{308}/A_{525})_{org}$ for a suspension in hexane, in the presence of CEMULSOL NP9, of the non-compatibilized nanoporous inorganic starting particles is equal to 2.5. The improvement in the dispersibility provided by the compatibilization is very low.

The compatibilized particles thus isolated exhibit an average hydrophobicity (their extraction by an organic phase is impossible) but good surface protection (+++) according to the colorimetric test.

Example 3

In this example, the particles to be treated are titanium oxide particles in lenticular anatase form (obtained by thermal hydrolysis of titanium oxychloride in the presence of citric acid). These polycrystalline particles (size of crystallite=6 nm) are 20 to 30 nm in diameter, and are thus well individualized. Porosity measurements showed that these lenticular anatase particles have pore sizes smaller than 5 nm.

In a first step, a pretreatment consisting in removing this nanoporosity is thus performed.

A base stock is prepared, in a reactor stirred at 500 revolutions/minute, by mixing, at 25° C., 240 ml of deionized water, 500 ml of pure ethanol, 260 ml of aqueous ammonia solution containing 25% of $NH_3$ and 10 g of titanium oxide.

The surface pretreatment is carried out by adding, at a flow rate of 15 ml/h, a solution containing 12 g of tetraethyl orthosilicate in 50 ml of ethanol. After the addition, a stable suspension is obtained.

The compatibilization is then carried out by adding, at a flow rate of 15 ml/h, a solution containing 5 g of octyltrimethoxysilane in 10 ml of ethanol. At the end of the reaction, a flocculated suspension is obtained which sediments in the reactor.

This suspension is left to mature for two hours with stirring.

It is then distilled under vacuum in order to remove the ethanol and the ammonia at a temperature of 70°–80° C. and at a pressure of 8 kPa (approximately 60 mmHg). When about 200 ml of distillate are collected, the reactor is allowed to cool, normal pressure is re-established and water is added to the reactor so as to readjust to the initial volume. These operations are then repeated in order to remove the residual ethanol and ammonia.

When the volume remaining in the reactor is only 500–600 ml, the mixture begins to foam, and the dispersion appears soapy and pearlescent. The mixture is then left to cool. The contents of the reactor are recovered.

The total load from the reactor is separated into two equal fractions which are centrifuged. The upper aqueous layer is allowed to separate by settling. The centrifugation cake is resuspended in 100 ml of absolute ethanol, mixed well and then centrifuged.

The upper layer is again separated by settling and the centrifugation cake is resuspended in 100 ml of absolute ethanol, mixed well and then centrifuged. The cake obtained is fairly compact and firm. It is left to dry in the air in order to obtain a powder.

The dispersibility of the compatibilized particles is characterized as in Example 1. For the organic suspension of compatibilized particles, the ratio $(A_{308}/A_{525})_{org}$ is equal to 26. For the aqueous sol of noncompatibilized starting particles, the ratio $(A_{308}/A_{525})_{aq}$ is equal to 30. The ratio $(A_{308}/A_{525})_{org}$ is close to $(A_{308}/A_{525})_{aq}$, which indicates that the dispersibility in organic medium of the compatibilized particles is excellent.

Example 4

This example illustrates a compatibilization process in a two-phase medium. The particles to be treated are the same as in Example 3, and they are first subjected to a pretreatment intended to remove the nanoporosity.

A base stock is prepared in a reactor stirred at 500 revolutions minute by mixing, at 25° C., 240 ml of deionized water, 500 ml of pure ethanol, 260 ml of aqueous ammonia solution containing 25% of $NH_3$ and 10 g of titanium oxide.

The surface pretreatment is carried out by adding, at a flow rate of 15 ml/h, a solution containing 12 g of tetraethyl orthosilicate in 50 ml of ethanol. At the end of the addition, a stable suspension is obtained.

The compatibilization is then performed in the presence of an immiscible supernatant organic phase.

80 ml of isopropyl palmitate are added to the suspension obtained above. A solution containing 4 g of octyltrimethoxysilane in 10 ml of ethanol is added at a flow rate of 15 ml/h, the addition taking place with stirring at 500 revolutions/minute.

After the addition, the contents of the reactor are heated at 60° C. for 7 hours. The organic layer then becomes milky. This phase consisting of compatibilized $TiO_2$ particles suspended in isopropyl palmitate is recovered.

Example 5

Cerium oxide particles are compatibilized.

A base stock is prepared in a reactor stirred at 500 revolutions/minute by mixing, at 25° C., 500 ml of deionized water, 500 ml of pure ethanol and 5 g of colloidal cerium hydrate. The pH of the aqueous-alcoholic suspension is adjusted to 3.5 with the required amount of sodium acetate.

A solution containing 1 g of octyltrimethoxysilane in 50 ml of ethanol is added to the base stock at a flow rate of 15 ml/h. A flocculated suspension is obtained which sediments in the reactor.

100 ml of isopropyl palmirate are poured into the flocculated suspension and, after stirring, the solid passes into the organic phase.

It was also possible to verify that the powder formed of the compatibilized particles of this example is hydrophobic.

Example 6

In this example, the particles to be treated are non-nanoporous silica particles.

In order to carry out the compatibilization, 279 g of a suspension of silica in water, containing 50 g of silica (i.e. 21.5% by weight) homogenized by ultrasound, are prepared. Since the operation is exothermic, the temperature of the suspension rises to about 60° C. and it is left to cool to room temperature before running it into a reactor equipped with a stirring system and an addition funnel. A base stock is prepared by adding thereto 306.7 g of 20% aqueous ammonia solution and 542 ml of absolute ethanol, with stirring at 500 revolutions/minute.

31.6 g of octyltrimethoxysilane dissolved in 92 ml of absolute ethanol are then introduced dropwise via the dropping funnel, while stirring the mixture. At the end of the addition, the mixture is matured such that the particles are in contact with the octyltrimethoxysilane for a total of 5 hours.

After the maturation, some of the mixture is withdrawn and placed in contact with isopropyl palmitate, and immediate migration of the particles to the organic phase is observed.

The remainder of the reaction mixture is centrifuged and separated after settling, and the centrifugation cake is taken up in 95% ethanol. This operation is carried out 3 times, as in Example 3.

The final cake obtained is air-dried to give 75 g of powder.

The particles thus compatibilized exhibit perfect hydrophobicity.

Example 7

The compatibilized titanium oxide particles of Example 2 are used as anti-UV agent in a polypropylene polymer.

0.1 to 0.2% by weight of $TiO_2$ particles is incorporated into polypropylene.

A film of this polymer 200 μm in thickness is formed. This film retains the transparency of the unfilled polymer.

The anti-UV action of these particles is satisfactory and comparable to that of organic anti-UV agents, introduced in a proportion of 0.1% by weight of the polymer.

For comparison, 0.1% by weight of titanium oxide of the "pigment for paint" type (particles 0.2 μm to 0.3 μm in diameter) is incorporated. A film 200 μm in thickness obtained with this polymer is white. In addition, these titanium oxide particles accelerate the degradation of the film.

I claim:

1. Organophilic metal oxide particles obtained by a process comprising the step of reacting
   (a) an aqueous-alcoholic suspension of metal oxide particles having no pores less than 5 nm in diameter on the surface thereof with
   (b) an anhydrous alcoholic solution consisting of an alcohol and at least one alkoxysilane of formula (1):

$$Si(OR)_xR'_{4-x} \qquad (1)$$

in which R is an alkyl of from 1 to 6 carbon atoms, R' is an alkyl, cycloalkyl, aryl, alkylaryl, arylalkyl, alkenyl or alkynyl, and x is an integer from 1 to 3, to obtain a mixture comprising said organophilic metal oxide particles, wherein said metal oxide particles are selected from the group consisting of alumina, transition metal oxides, and rare-earth metal oxides.

2. A suspension comprising the organophilic metal oxide particles according to claim 1, wherein the reaction of (a) and (b) is carried out in the presence of a water-immiscible organic liquid, and wherein said metal oxide particles migrate into said water-immiscible organic liquid as they are compatibilized.

3. A suspension comprising the organophilic metal oxide particles according to claim 1, wherein said mixture comprising the organophilic metal oxide particles is separated into a liquid and solid particles, and the solid particles are washed with an alcohol and then dried, and wherein (i) said dried solid particles are suspended in an organic solvent selected from the group consisting of a natural or synthetic oil, a hydrocarbon solvent and a water-immiscible solvent to form a suspension comprising the organophilic metal oxide particles, and (ii) a stabilizing agent selected from the group consisting of non-ionic surfactants is added to the suspension.

4. A suspension comprising the organophilic metal oxide particles according to claim 1, wherein said mixture comprising the organophilic metal oxide particles is stirred in an organic solvent selected from the group consisting of a natural or synthetic oil, a hydrocarbon solvent and a water-immiscible solvent, whereby the organophilic metal oxide particles in the mixture pass into the organic solvent to form a suspension, and wherein a stabilizing agent selected from the group consisting of non-ionic surfactants is added to the suspension.

5. A process for the preparation of organophilic metal oxide particles, said process comprising reacting (a) an aqueous-alcoholic suspension of metal oxide particles having no pores less than 5 nm in diameter on the surface thereof with (b) an anhydrous alcoholic solution comprising at least one alkoxysilane of formula (1):

$$Si(OR)_xR'_{4-x} \qquad (1)$$

in which R is an alkyl of from 1 to 6 carbon atoms, R' is an alkyl, cycloalkyl, aryl, alkylaryl, arylalkyl, alkenyl or alkynyl, and x is an integer from 1 to 3, to obtain a mixture comprising said organophilic metal oxide particles, wherein said metal oxide particles are selected from the group consisting of alumina, transition metal oxides, and rare-earth metal oxides, and wherein the aqueous-alcoholic suspension (a) and the anhydrous alcoholic solution (b) comprise $C_1$–$C_5$ alcohols which are the same or different.

6. The process according to claim 5, wherein said metal oxide particles are $TiO_2$.

7. The process according to claim 5, wherein said metal oxide particles are $CeO_2$.

8. The process according to claim 5, wherein said metal oxide particles have a mean diameter of less than or equal to 100 nm.

9. The process according to claim 5, further comprising a preliminary step of treating nanoporous metal oxide particles to obtain said metal oxide particles having no pores less than 5 nm in diameter on the surface thereof.

10. The process according to claim 9, wherein said preliminary step comprises reacting an aqueous-alcoholic suspension of said nanoporous metal oxide particles with at least one tetraalkoxysilane of formula (2):

$$Si(OR")_4 \qquad (2)$$

in which R" is an alkyl of from 1 to 5 carbon atoms, to obtain said aqueous-alcoholic suspension (a).

11. The process according to claim 10, wherein the reaction of (a) and (b) is carried out in the presence of a water-immiscible organic liquid, and wherein said metal oxide particles migrate into said water-immiscible organic liquid as they are compatibilized.

12. The process according to claim 9, wherein said preliminary step comprises heat treating said nanoporous metal oxide particles in an autoclave.

13. The process according to claim 5, wherein R is a methyl or ethyl group.

14. The process according to claim 5, wherein R' is an octyl, dodecyl or octadecyl group.

15. The process according to claim 5, wherein x is 3.

16. The process according to claim 5, wherein the weight ratio of the alkoxysilane of formula (1) to the metal oxide particles is between 1 and 60%.

17. The process according to claim 5, wherein said aqueous-alcoholic suspension (a) has a weight ratio of water to alcohol of between 0.2 to 0.8.

18. The process according to claim 5, wherein the alcohol in the aqueous-alcoholic suspension (a) and the alcohol in the anhydrous alcoholic solution (b) are the same.

19. The process according to claim 5, wherein the aqueous-alcoholic suspension (a) has a pH between 1 and 5.

20. The process according to claim 5, wherein the aqueous-alcoholic suspension (a) has a pH between 9 and 12.

21. The process according to claim 5, wherein the aqueous-alcoholic suspension (a) comprises from 5 g/l to 200 g/l of said metal oxide particles.

22. The process according to claim 5, wherein the reaction of (a) and (b) is carried out at a temperature of 15° to 70° C.

23. The process according to claim 5, wherein the reaction of (a) and (b) is carried out at room temperature.

24. The process according to claim 5, further comprising separating said mixture comprising said organophilic metal oxide particles into a liquid and solid particles, washing said solid particles with an alcohol, and drying said washed solid particles.

25. A process for the preparation of an organic suspension comprising organophilic metal oxide particles, said process comprising the steps of:

(i) carrying out the process according to claim 24;

(ii) suspending the dried solid particles in an organic solvent selected from the group consisting of a natural or synthetic oil, a hydrocarbon solvent, and a water-immiscible solvent to obtain an organic suspension comprising organophilic metal oxide particles; and (iii) adding a stabilizing agent selected from the group consisting of non-ionic surfactants to said organic suspension.

26. A process for the preparation of an organic suspension comprising organophilic metal oxide particles, said process comprising the steps of:

(i) carrying out the process according to claim 5;

(ii) stirring said mixture comprising said organophilic metal oxide particles with an organic solvent selected from the group consisting of a natural or synthetic oil, a hydrocarbon solvent and a water-immiscible solvent, whereby the organophilic metal oxide particles pass into the organic solvent to form an organic suspension; and (iii) adding a stabilizing agent selected from the group consisting of non-ionic surfactants to said organic suspension.

27. A method for protecting plastics from UV radiation, said method comprising incorporating an effective amount of the organophilic metal oxide particles produced according to claim 5 in said plastics.

28. A method of protecting plastics from UV radiation, said method comprising incorporating an effective amount of the organophilic metal oxide particles produced according to claim 6 in said plastics.

29. A method of protecting plastics from UV radiation, said method comprising incorporating an effective amount of the organophilic metal oxide particles produced according to claim 7 in said plastics.

30. A method of protecting plastics from UV radiation, said method comprising incorporating an effective amount of the organophilic metal oxide particles produced according to claim 12 in said plastics.

31. A method for protecting liquid or solid organic cosmetic products from UV radiation, said method comprising incorporating an effective amount of the organophilic metal oxide particles produced according to claim 5 in said cosmetic products, wherein said organophilic metal oxide particles are selected from the group consisting of organophilic cerium oxide particles and organophilic titanium oxide particles.

32. A method of protecting liquid or solid organic cosmetic products from UV radiation, said method comprising incorporating an effective amount of the organophilic metal oxide particles produced according to claim 6 in said cosmetic products.

33. A method of protecting liquid or solid organic cosmetic products from UV radiation, said method comprising incorporating an effective amount of the organophilic metal oxide particles produced according to claim 7 in said cosmetic products.

34. A method of protecting liquid or solid organic cosmetic products from UV radiation, said method comprising incorporating an effective amount of the organophilic metal oxide particles produced according to claim 12 in said cosmetic products, wherein said organophilic metal oxide particles are selected from the group consisting of organophilic cerium oxide particles and organophilic titanium oxide particles.

* * * * *